(12) United States Patent
Magniette

(10) Patent No.: US 9,846,151 B2
(45) Date of Patent: Dec. 19, 2017

(54) SAMPLE VIAL FOR DIGITAL HOLOGRAPHIC ANALYSIS OF A LIQUID CELL SAMPLE

(71) Applicant: Ovizio Imaging Systems NV/SA, Brussels (BE)

(72) Inventor: Olivier Magniette, Deurle (BE)

(73) Assignee: Ovizio Imaging Systems NV/SA, Brussels (BE)

(*) Notice: Subject to any disclaimer, the term of this patent is extended or adjusted under 35 U.S.C. 154(b) by 188 days.

(21) Appl. No.: 14/359,556

(22) PCT Filed: Nov. 20, 2012

(86) PCT No.: PCT/EP2012/073116
§ 371 (c)(1),
(2) Date: May 20, 2014

(87) PCT Pub. No.: WO2013/076082
PCT Pub. Date: May 30, 2013

(65) Prior Publication Data
US 2014/0349336 A1     Nov. 27, 2014

(30) Foreign Application Priority Data

Nov. 21, 2011  (EP) .................................... 11189986

(51) Int. Cl.
*G01N 33/487* (2006.01)
*G01N 21/03* (2006.01)
(Continued)

(52) U.S. Cl.
CPC ... *G01N 33/48778* (2013.01); *A61B 10/0291* (2013.01); *B01L 3/502* (2013.01);
(Continued)

(58) Field of Classification Search
None
See application file for complete search history.

(56) References Cited

U.S. PATENT DOCUMENTS 4,786,594 A   11/1988   Khanna et al.
5,089,416 A   2/1992    Schwartz
(Continued)

FOREIGN PATENT DOCUMENTS

CN   202 808 799     3/2013
EP      0479231 A1   4/1992
(Continued)

OTHER PUBLICATIONS

Indebetouw, G. et al. Feb. 20, 2007. Scanning holographic microscopy with resolution exceeding the Rayleigh limit of the objective by superposition of off-axis holograms. Applied Optics 46(6): 993-1000. specif. pp. 993, 994.*
(Continued)

*Primary Examiner* — Renee Claytor
*Assistant Examiner* — Sharon M Papciak
(74) *Attorney, Agent, or Firm* — Knobbe Martens Olson & Bear, LLP

(57) ABSTRACT

The current invention concerns a sample vial for receiving a liquid cell sample, to be used in conjunction with a digital holographic microscope (DHM), said sample vial comprises at least two compartments in fluid connection with one another, said compartments comprising at least one pair of screening surfaces, said screening surfaces are essentially flat; and characterized in that the distance between the pair of screening surfaces of the second compartment is smaller than the distance between the pair of screening surfaces of the first compartment. In a second and third aspect, the current invention pertains to a method and system for
(Continued)

analyzing a liquid cell sample by DHM, employing the sample vial of the current invention.

15 Claims, 10 Drawing Sheets

(51) Int. Cl.
| | | |
|---|---|---|
| G01N 33/574 | (2006.01) | |
| G01N 1/40 | (2006.01) | |
| G03H 1/00 | (2006.01) | |
| B01L 3/00 | (2006.01) | |
| A61B 10/02 | (2006.01) | |
| G03H 1/04 | (2006.01) | |

(52) U.S. Cl.
CPC ............ *B01L 3/5082* (2013.01); *G01N 1/405* (2013.01); *G01N 21/03* (2013.01); *G01N 33/57411* (2013.01); *A61B 2010/0216* (2013.01); *B01L 2200/0647* (2013.01); *B01L 2200/0652* (2013.01); *B01L 2300/023* (2013.01); *B01L 2300/042* (2013.01); *B01L 2300/0609* (2013.01); *B01L 2300/0681* (2013.01); *B01L 2300/0803* (2013.01); *B01L 2300/0832* (2013.01); *B01L 2300/0851* (2013.01); *B01L 2300/0858* (2013.01); *B01L 2400/086* (2013.01); *G03H 1/0443* (2013.01); *G03H 2001/005* (2013.01)

(56) References Cited

U.S. PATENT DOCUMENTS

| | | | |
|---|---|---|---|
| 5,243,409 A | 9/1993 | Sagner | |
| 5,256,571 A | 10/1993 | Hurley et al. | |
| 5,495,333 A | 2/1996 | Konda | |
| 6,249,345 B1 | 6/2001 | Kraack | |
| 6,327,377 B1 | 12/2001 | Rutenberg | |
| 6,361,934 B1* | 3/2002 | Acton | A01N 1/02 128/898 |
| 6,394,966 B1* | 5/2002 | Gill | A61B 10/0045 600/569 |
| 6,651,008 B1 | 11/2003 | Vaisberg et al. | |
| 6,809,862 B2 | 10/2004 | Behnsen et al. | |
| 6,924,094 B1 | 8/2005 | Gingeras et al. | |
| 6,954,667 B2 | 10/2005 | Treado | |
| 7,286,222 B2 | 10/2007 | Gardner | |
| 7,616,320 B2 | 11/2009 | Javidi et al. | |
| 2002/0106119 A1 | 8/2002 | Foran | |
| 2002/0164063 A1 | 11/2002 | Heckman | |
| 2003/0113832 A1* | 6/2003 | Lauf | C12M 35/02 435/29 |
| 2003/0199649 A1 | 10/2003 | Orbison et al. | |
| 2005/0036181 A1 | 2/2005 | Marquet et al. | |
| 2005/0272103 A1 | 12/2005 | Chen | |
| 2006/0014239 A1 | 1/2006 | Luttmann et al. | |
| 2006/0088814 A1 | 4/2006 | Hecht et al. | |
| 2006/0132799 A1 | 6/2006 | Dubois et al. | |
| 2006/0283945 A1* | 12/2006 | Excoffier | B01L 3/5457 235/439 |
| 2007/0216906 A1 | 9/2007 | Javidi et al. | |
| 2008/0018966 A1 | 1/2008 | Dubois et al. | |
| 2008/0032325 A1 | 2/2008 | DiMarzio | |
| 2008/0242556 A1 | 10/2008 | Cao et al. | |
| 2009/0082637 A1 | 3/2009 | Galperin | |
| 2009/0092227 A1 | 4/2009 | David | |
| 2009/0244667 A1 | 10/2009 | Frentz | |
| 2009/0296083 A1 | 12/2009 | Saski et al. | |
| 2009/0305393 A1 | 12/2009 | Joeris | |
| 2010/0034442 A1 | 2/2010 | Minakuchi | |
| 2010/0196871 A1* | 8/2010 | Dodgson | A61D 19/022 435/1.1 |
| 2010/0315501 A1 | 12/2010 | Ludwig | |
| 2011/0134426 A1 | 6/2011 | Kaduchak | |
| 2011/0204256 A1 | 8/2011 | Patt | |
| 2011/0212440 A1 | 9/2011 | Viovy et al. | |
| 2012/0015391 A1 | 1/2012 | Zhang et al. | |
| 2012/0200901 A1 | 8/2012 | Dubois | |
| 2012/0218379 A1 | 8/2012 | Ozcan | |
| 2014/0038171 A1 | 2/2014 | Metzger et al. | |
| 2014/0139625 A1 | 5/2014 | Mathuis et al. | |
| 2014/0193850 A1 | 7/2014 | Jooris et al. | |
| 2014/0195568 A1 | 7/2014 | Mathuis et al. | |
| 2014/0329231 A1 | 11/2014 | Magniette | |
| 2015/0056607 A1 | 2/2015 | Jooris et al. | |
| 2015/0248109 A1 | 9/2015 | Mathuis et al. | |
| 2016/0184817 A1 | 6/2016 | Jooris et al. | |

FOREIGN PATENT DOCUMENTS

| | | |
|---|---|---|
| EP | 1524491 A1 | 4/2005 |
| EP | 2008715 A1 | 12/2008 |
| WO | WO 98/57152 | 12/1998 |
| WO | WO 99/44593 A1 | 9/1999 |
| WO | WO 2004/057464 A2 | 7/2004 |
| WO | WO 2004/102111 A1 | 11/2004 |
| WO | WO 2006/047252 A1 | 5/2006 |
| WO | WO 2007/073345 A1 | 6/2007 |
| WO | WO 2009/051741 A2 | 4/2009 |
| WO | WO 2009/151632 | 12/2009 |
| WO | WO 2009/154558 A1 | 12/2009 |
| WO | WO 2011/042442 A1 | 4/2011 |
| WO | WO 2011/068764 A2 | 6/2011 |
| WO | WO 2011/099925 A1 | 8/2011 |
| WO | WO 2011/154143 A1 | 12/2011 |
| WO | WO 2013/120886 A1 | 8/2013 |
| WO | WO 2014/044823 A1 | 3/2014 |

OTHER PUBLICATIONS

Kemper, B. et al. Feb. 1, 2008. Digital holographic microscopy for live cell applications and technical inspection. Applied Optics 47(4): A52-A61. specif. pp. A52, A53, A56, A59.*
Beitsch et al., "Detection of carcinoma cells in the blood of breast cancer patients," The American Journal of Surgery, vol. 180, pp. 446-449 (Dec. 2000).
Boulet et al., "Cancer Epidemiology," Biomarkers & Prevention, 2008, 17(4): 810-817.
Daneshpanah et al., "3D Holographic Imaging and Trapping for Non-Invasive Cell Identification and Tracking," Journal of Display Technology, vol. 6(10), pp. 490-499 (Oct. 2010).
Extended European Search Report for European Patent Application No. 16151897.2, dated Jul. 21, 2016.0.
Fook Chiong Cheong et al. "Flow visualization and flow cytometry with holographic video microscopy", Proceedings of the SPIE— The International Society for Optical Engineering SPIE—The International Society for Optical Engineering USA, vol. 7619, 2010, XP040518833, ISSN: 0277-786X. Published Feb. 10, 2010.
Frank Dubois et al. "Applications of digital holographic microscopes with partially spatial coherence sources", Journal of Physics: Conference Series, Institute of Physics Publishing, Bristol, GB, vol. 139, No. 1, p. 12027, XP020148183, ISSN: 1742-6596. Published Nov. 1, 2008.
Fu et al., "Quantitative DIC microscopy using an off-axis self-interference approach," Optics Letters, vol. 35(14), pp. 2370-2372 (Jul. 15, 2010).
Kemper et al., "Monitoring of laser micro manipulated optically trapped cells by digital holographic microscopy," J Biophoton, vol. 3(7), pp. 425-431 (2010).
Kemper et al., "Investigation of living pancreas tumor cells by digital holographic microscopy," Journal of Biomedical Optics, vol. 11(3), pp. 034005-1-034005-8 (May/Jun. 2006).
Kemper et al., "Simplified approach for quantitative digital holographic phase contrast imaging of living cells," Journal of Biomedical Optics, vol. 16(2), pp. 026014-1-026014-4 (Feb. 2011).
Kemper et al., "Self interference digital holographic microscopy approach for inspection of technical and biological phase specimens," Proceedings of the SPIE—The International Society for

(56) References Cited

OTHER PUBLICATIONS

Optical Engineering SPIE—The International Society for Optical Engineering USA, vol. 8082, May 23, 2011.

Lee et al., "Incremental feature weight learning and its application to a shape-based query system," Pattern Recognition Letters, vol. 23, pp. 865-874 (2002).

Marin et al., "A meta-index for querying distributed moving object database servers," Information Systems, vol. 35, pp. 637-661 (2010).

McClatchey et al., "Object Databases in a Distributed Scientific Workflow Application," Information Technology, 1997, BIWIT '97., Proceedings of the Third Basque International Workshop on Biarritz, France, Jul. 2-4, 1997; Los Alamitos, CA, USA, IEEE Comput. Soc. US, Jul. 2, 1997, pp. 11-21.

Mihailescu M et al. "Microchannel-pinhole parameters investigation for cells visualization in holographic microscopy", Semiconductor Conference (CAS), 2011 International, IEEE pp. 75-78, XP032069149, DOI: 10.1109/SMICND.2011.6095718 ISBN: 978-1-61284-173-1. Published Oct. 17, 2011.

Moon et al., "Automated Three-Dimensional Identification and Tracking of Micro/Nanobiological Organisms by Computational Holographic Microscopy," Proceedings of the IEEE, vol. 97(6), pp. 990-1010 (Jun. 2009).

Nenadic et al., "A Possibility of Applying Differential Digital Holography in Manufacturing Process," 48th International Symposium ELMAR-2006, Jun. 7-9, 2006, Zadar, Croatia, pp. 103-106.

Owens et al., "Distinguishing Prostatic from Colorectal Adenocarcinoma on Biopsy Samples, The Role of Morphology and Immunohistochemistry," Arch Pathol Lab Med, vol. 131, pp. 599-603 (Apr. 2007).

Sahasranuddhe et al., Future Microbiol., 2011 6(9):1-25.

Sun et al., "Visualization of fast-moving cells in vivo using digital holographic video microscopy," Journal of Biomedical Optics, vol. 13(1), pp. 014007-1-014007-9 (Jan./Feb. 2008).

Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar. 18, 2009).

Weigum et al., "Nano-Bio-Chip Sensor Platform for Examination of Oral Exfoliative Cytology," Cancer Prevention Research, vol. 3, pp. 518-528 (2010).

White et al., "Isolation of Stool-Derived Mucus Provides a High Yield of Colonocytes Suitable for Early Detection of Colorectal Carcinoma," Cancer Epidemiol Biomarkers Prev, vol. 8, pp. 2006-2013 (2009).

Yong-Seok Choi et al. "Lateral and cross-lateral focusing of spherical particles in a square microchannel", Lab on a Chip, vol. 11, No. 3, pp. 460-465, XP55032064, ISSN: 1473-0197, DOI: 10.1039/c0lc00212g. Published Feb. 1, 2011.

Zhou et al., "An Image Clustering and Retrieval Framework Using Feedback-based Integrated Region Matching," 2009 International Conference on Machine Learning and Applications, 2009, ICMLA '09, IEEE, Piscataway, New Jersey, USA, Dec. 13, 2009, pp. 596-601.

International Search Report—PCT/EP2014/066312—ISA/EPO—dated Jan. 10, 2014.

\* cited by examiner

SAMPLE VIAL FOR DIGITAL HOLOGRAPHIC ANALYSIS OF A LIQUID CELL SAMPLE

CROSS-REFERENCE TO RELATED APPLICATIONS

This application is the U.S. National Phase under 35 U.S.C. §371 of International Application PCT/EP2012/073116, filed Nov. 20, 2012, which claims priority to EP 11189986.0, filed Nov. 21, 2011.

TECHNICAL FIELD

The invention pertains to the technical field of cell analysis by digital holographic microscopy (DHM). More specifically, the current invention discloses a sample vial, specifically designed to be used in conjunction with DHM, for the analysis of a liquid cell sample. In a further aspect, the invention pertains a method and system for liquid cell analysis.

BACKGROUND

Digital Holographic Microscopy (DHM) is a technique which allows a recording of a 3D sample or object without the need of scanning the sample layer-by-layer. Numerous parameters related to the scanned object or sample can be obtained by digital holographic microscopy. Digital holographic microscopy has been proven to be particularly useful for analyzing living transparent objects such as cells or samples containing cells. Such samples have for a long time been studied by means of light microscopy, such as fluorescence, confocal of phase contrast microscopy. However, the latter techniques often require treatment of the cells, such as fixation of the cells and/or staining with markers or fluorescent dyes. As such, these treatments might result in loss of information stored in the cell. Moreover, these treatments are time consuming and require specific training and knowledge of personnel. Digital holographic microscopy omits the necessity of treating the cells prior to analysis. Furthermore, DHM allows for the analysis of cells in a liquid sample, again omitting certain handlings, such as for instance depositing cells on a microscopic plate in order to achieve a thin layer of cells. As such, DHM is an emerging new tool used for cell sample analysis, for instance in the diagnostic field.

In order to study a liquid cell sample by DHM, one has to provide the cell sample in a sample vial, optimized for use in conjunction of a DHM. The purpose is to provide a vial that allows accurate phase and amplitude information of a cell sample and its cells, through use of a DHM. WO 2009 154 558 discloses a method for analyzing cells in a sample through DHM and a sample vial to be used in conjunction with a digital holographic microscope. The sample vial is specifically designed as a culture flask for growing cells, and is hence less suited to be used as a sample vial for diagnostic purpose. As samples obtained for diagnostic purpose often have a variable cell concentration, different from sample to sample, it is often difficult to obtain the right cell concentration or in case of samples comprising few cells, to analyze an adequate amount of cells in order to come to a reliable and statistically significant analysis of the sample. Furthermore, as cells in a suspension obtained for diagnostic purpose are freely floating in the sample, it is not always easy to obtain a qualitative image and analysis of the cells in the sample. It is the object of the current invention to provide a solution for at least one of the problems mentioned above.

SUMMARY OF THE INVENTION

The present invention provides for a sample vial for receiving a liquid cell sample to be used in conjunction with a digital holographic microscope (DHM), according to claim 1. Preferably, said sample vial comprises at least two compartments in fluid connection with one another, said compartments comprising at least one pair of screening surfaces, said screening surfaces are essentially flat; and characterized in that the distance between the pair of screening surfaces of the second compartment is smaller than the distance between the pair of screening surfaces of the first compartment. The latter ensures different cell densities in the different compartments of said sample vial, allowing choosing the optimal field of view for said analysis by DHM, dependent on the cell sample and purpose of the analysis. Furthermore, by choosing an optimal height of the second compartment, the cells, normally freely floating in the solution, will become immobilized in the second compartment in a very short amount of time, allowing a gain optimal screening.

A sample vial according to claim 1, whereby said ratio of the distance between said pair of screening surfaces of said first compartment and said pair of screening surfaces of second compartment comprises between 200:1 and 20:1, preferably 80:1, more preferably 40:1 and/or the ratio of the surface area of a screening surface of the first compartment and a screening surface of the second compartment comprises between 1:100 and 10:1. The latter ratios are optimized to ensure achieving different cell densities in the two compartments of the sample vial, in order to come to an adequate screening and analysis by DHM. The chosen ratio's will depend on the nature of the cells and the purpose of the analysis. Preferably said screening surfaces comprise an optically transparent material.

In another preferred embodiment, said vial comprises a lid, making vial liquid-tight when engaged to said vial. Said lid comprises an optically transparent material whereby said material is only optically transparent for light with wavelengths equal to these from the illumination means of DHM and partially or not optically transparent for light with other wavelengths. The latter allows transmission of said illumination beam of DHM and illumination of said sample inside liquid-tight vial.

In yet another embodiment, said first compartment comprises an entrance for receiving a cell collecting device. The latter provides for an ease of handling, avoids risk of losing collected cell sample and a maximized time management, as the collected cell sample can be immediately transferred from the site or origin of collection to the sample vial used for analysis of the sample.

Preferably, a fluid connection between said compartments prevents said cell collecting device from entering said second compartment. The latter ensures that the cell collection device will not cause disturbance when screening the cell sample in the second compartment.

In a preferred embodiment, said vial comprises means for aiding the disengagement of means for collecting cells from said cell collection device. These means help the practitioner to exactly position the cell collection device as well as to provide help with the exertion of force on the handle of the cell collection device needed for disengaging the means for collecting cells from the cell collection device.

Preferably, said first compartment comprises a sub-compartment for receiving means for collecting cells. Said sub-compartment avoids interference of said means for collecting cells during DHM analysis.

In another preferred embodiment, said vial comprises supporting means at the base. The supporting means avoid scratching and/or staining of the screening surfaces of the vial, causing interference during the screening.

Preferably, said vial comprises identification means, preferably an RFID tag. More preferably, said vial comprises a preservative.

In another preferred embodiment, said vial is internally provided with a filter membrane. The filter membrane may form an internal barrier, allowing passage of liquid and cells, but blocking unwanted cell debris, mucus and tissue clumps.

In a second aspect, the current invention provides for a method for analyzing a liquid cell sample by digital holographic microscopy (DHM) according to claim 14. Said method comprises the steps of
    obtaining a cell sample;
    preserving said cell sample in a sample vial according to the present invention;
    providing a digital holographic microscope;
    obtaining parameters and images of cell sample by means of DHM,
characterized in that said DHM obtains parameters and images by screening said sample in the first and/or second compartment of said vial via a scanning pattern. The latter ensures that only unique sections of said sample will be scanned by DHM, hence preventing that one section is screened multiple times. The latter ensures that significantly reliable and adequate information is obtained from said cell sample.

In a final aspect, the invention provides for a system for analyzing a liquid cell sample according to claim 15. Said system comprises a digital holographic microscope and at least one sample vial as disclosed in the current invention, characterized in that system comprises means for screening said sample via a scanning pattern.

DETAILED DESCRIPTION OF THE INVENTION

Figure 1A:
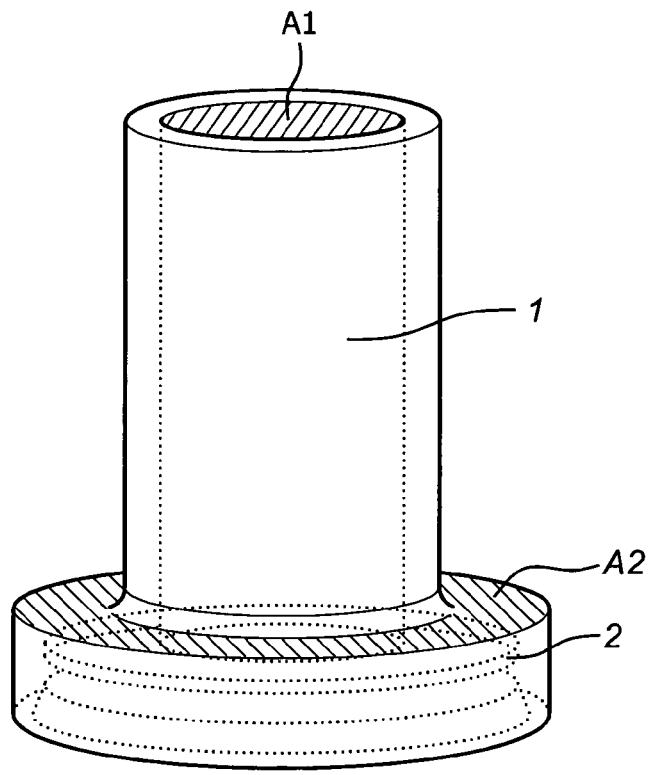
FIGS. 1-7 and 9 depict various embodiments of the sample vial according to the current invention.

The present invention concerns a method for analysing a liquid cells sample by DHM and a sample vial to be used in conjunction with DHM. The cell samples are analysed in a non-destructive manner and information is provided on the cells present in the sample.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the invention provides a sample vial for receiving a liquid cell sample, to be used in conjunction with a digital holographic microscope (DHM), said sample vial comprises at least two compartments in fluid connection with one another, said compartments comprising at least one pair of screening surfaces, said screening surfaces are essentially flat;

Preferably, said distance between the pair of screening surfaces of the second compartment is smaller than the distance between the pair of screening surfaces of the first compartment.

The term "cell sample" as used herein refers to any specimen obtained from a biological organism, preferably a living organism, which comprises cells from said biological organism. The term relates also to specimen obtained from non-living, i.e. dead biological organisms, in particular recently deceased organisms. In preferred embodiments of the present invention a cell sample may be derived from an animal, preferably from a mammal, e.g. from a cat, a dog, a swine, a horse, a cattle, a sheep, a goat, a rabbit, a rat, a mouse, a monkey. Particularly preferred is a sample obtained from a human being.

In one embodiment said cell sample is a tissue sample, a biopsy sample, a blood sample, a serum sample, a brushing or scraping sample from oral cavities, nipple secretions, skin lesions, and eye brushings, a fine-needle-aspiration sample, a smear sample, a mucoid specimens taken from respiratory and gastrointestinal tracts and body fluids such as serous effusions or urinary or cerebrospinal fluids.

In a preferred embodiment, said sample is a smear sample.

In another preferred embodiment, said smear sample is a cervical sample.

Digital Holographic Microscopy (DHM) is a technique which allows a recording of a 3D sample or object without the need of scanning the sample layer-by-layer. In this respect DHM is a superior technique to confocal microscopy. In DHM, a holographic representation is recorded by a digital camera such as a CCD- or a CMOS-camera, which can subsequently be stored or processed on a computer.

To make a holographic representation, or hologram, traditionally a highly coherent or a partially coherent light source such as laser-light, is used to illuminate the sample. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM) is disclosed in European patent EP 1 631 788. DDHM is different to the other techniques in that it does not really make use of reference and object beams. In a preferred set-up of DDHM, the sample is illuminated by illumination means which consist of at least partially coherent light in reflection or in transmission mode. The reflected or transmitted sample beam can be sent through an objective lens and subsequently split in two by a beam splitter and sent along different paths in a differential interferometer, e.g. of the Michelson or Mach-Zehnder type. In one of the paths, a beam-bending element or tilting means is inserted, e.g. a transparent wedge. The two beams are then made to interfere with each other in the focal plane of a focusing lens and the interference pattern in this focal plane is recorded digitally and stored by e.g. a CCD-camera connected to a computer. Hereby, due to the beam-bending element, the two beams are slightly shifted in a controlled way and the interference pattern depends on the amount of shifting. Then the beam-bending element is turned, thereby altering the amount of shifting. The new interference pattern is also recorded. This can be done a number N of times, and from these N interference patterns, the gradient (or spatial derivative) of the phase in the focal plane of the focusing lens can be approximately computed. This is called the phase-stepping method, but other methods of obtaining the phase gradient are also known, such as a Fourier transform data processing technique. The gradient of the phase can be integrated to give the phase as a function of position. The amplitude of the light as a function of position can be computed from the possibly but not necessarily weighted average of the amplitudes of the N recorded interference patterns. Since phase and amplitude are thus known, the same information is obtained as in a direct holographic method (using a reference and an object beam), and a subsequent 3D reconstruction of the object can be performed.

The DHM used in the current invention can comprise a conventional digital holographic microscope (DHM), or a differential digital holographic microscope (DDHM). It is to be understood that the use of the term DHM in the current application implies all types of digital holographic microscopes, and is not merely limited to conventional DHM.

The use of DHM in a diagnostic setting has many advantages which makes it the ideal technique to implement in a diagnostic setting such as in the current invention. Besides a bright field image, a phase shift image is created as well. The phase shift image is unique for DHM and gives quantifiable information about optical distance. In reflection DHM, the phase shift image forms a topography image of the object.

Transparent objects, like living biological cells, are traditionally viewed in a phase contrast microscope or in a differential interference contrast microscope. These methods visualize phase shifting transparent objects by distorting the bright field image with phase shift information. Instead of distorting the bright field image, transmission DHM creates a separate phase shift image showing the optical thickness of the object. Digital holographic microscopy thus makes it possible to visualize and quantify transparent objects and is therefore also referred to as quantitative phase contrast microscopy. More so, DHM allows imaging subcellular structures in three dimensions.

A sample image is calculated at a given focal distance. However, as the recorded hologram contains all the necessary object wave front information, it is possible to calculate the object at any focal plane by changing the focal distance parameter in the reconstruction algorithm. In fact, the hologram contains all the information needed to calculate a complete image stack. In a DHM system, where the object wave front is recorded from multiple angles, it is possible to fully characterize the optical characteristics of the object and create tomography images of the object. Furthermore, as DHM systems do not have an image forming lens, traditional optical aberrations do not apply to DHM. Optical aberrations are "corrected" by design of the reconstruction algorithm. A reconstruction algorithm that truly models the optical setup will not suffer from optical aberrations. In optical microscopy systems, optical aberrations are traditionally corrected by combining lenses into a complex and costly image forming microscope objective. Furthermore, the narrow focal depth at high magnifications requires precision mechanics. Lastly, the needed components for a DHM system are inexpensive optics and semiconductor components, such as a laser diode and an image sensor. The low component cost in combination with the auto focusing capabilities of DHM, make it possible to manufacture DHM systems for a very low cost.

The term 'screening surfaces' as used in current invention is to be understood of the specific area of the vial which is at the inner side of the vial in contact with the sample and whereby said area is suitable for passage of a light beam in order to create a hologram of the sample.

As used herein, the distance between the pair of screening surfaces is to be understood as the inner-distance measured at the inside of said sample vial between two opposite points of said pair of screening surfaces. Preferably, especially for the second compartment, said opposite points of pair of screening surfaces are, when vial is filled with a sample, in contact with said sample. Preferably, said distance is the shortest distance that can be measured between two opposite points of said pair of screening surfaces (see FIG. 2a).

By making the distance of the screening surfaces of the first compartment larger than the distance of the screening surfaces of the second compartment, one can establish different cell densities within the same vial. Obtaining an optimal cell density is from crucial importance when wanting to analyse cells, especially from a suspension, when cells are mostly free-floating cells in a liquid cell sample. When said sample vial is immobile, allowing cells to settle by gravitation, typically more dense concentrations of cells will be found at the centre of the bottom of the first compartment compared to the cell density in the second compartment, whereby the nature of the cell density is determined by the distance between the pair of screening surfaces of each compartment. Typically, the density obtained in the second compartment, will closely mimic the cell density that is obtained with thin cell layer techniques, whereby cells originating from a liquid cell sample are deposited on an analytical carrier such as a microscope slide by for instance centrifugation forces or gravity force. The current sample vial omits all handling steps which precede the acquirement of such a thin cell layer, hence gaining time and money. Alternatively, when said sample vial is subjected to a rotational movement, preferably along a vertical axis of the vial, the cell density may be higher at the periphery of the first compartment and in the second compartment of the vial. The sample vial according the current invention provides for at least two different cell densities within the same sample vial. The chosen distance between each pair of screening surfaces of each compartment will vary according to the type of cell sample that is to be analyzed and is linked to the minimal cell density known to be required for analyzing such a cell sample. Simultaneously, the nature of the cell sample as well as the purpose of the analysis will define which pair of screening surfaces is to be used for the analysis by DHM. For instance, when a cell sample is composed of various sorts of cells, whereby only a specific subset of cells is important to the analysis, one can deduct in which compartment the latter are enriched, hence only focusing on that specific compartment. When the purpose of the analysis requires a high cell density of cells, screening can be performed through the pair of screening surfaces of said compartment with the highest distance between the latter, typically at the center of the bottom of the first compartment. Focusing on the compartment with the highest cell density will furthermore also limit the amount of images or fields of view required for coming to an adequate and significant analysis. Alternatively, when the cells in this field are too dense to perform an adequate analysis, and a high transparency is desired, screening can be performed through the pair of screening surfaces of the second compartment, in the situation where the sample vial is immobile. Again, the latter will depend on the nature of the cell sample, the cell quantity required for an optimal cell analysis and the purpose of the analysis. Furthermore, by applying the distant-ratio's as disclosed herein, cells will become immobilized in the second compartment of the vial in a very short amount of time, usually within seconds. This is of an enormous importance, since the current invention deals with cells which are freely moving within a solution. The latter is to be avoided when screening the cells with DHM, as it can cause disturbed imaging and a problematic analysis. By providing a compartment whereby the cells are essentially immobilized in an instant, the latter is avoided.

In a preferred embodiment, said ratio of the distance between said pair of screening surfaces of said first compartment and said pair of screening surfaces of second compartment comprises between 200:1 and 20:1, preferably 80:1, more preferably 40:1. The latter are optimized for the screening of various types of cell samples by DHM and for acquiring optimal cell densities in the compartments of the sample vial. The exact chosen ratio of the distances within these margins will entirely depend on the nature of the cell sample, the cells present in said cell sample which are to be analyzed and the purpose of the analysis. For each of these requirements, an optimal ratio is determined.

In a more preferred embodiment, said the ratio of the surface area of a screening surface of the first compartment and a screening surface of the second compartment comprises between 1:1000 and 50:1, preferably between 1:100 and 10:1, more preferably 1:10, most preferably 1:3. The latter ratio's are equally optimized for acquiring optimal cell densities in the compartments of the vial and for a representative scanning by DHM. Again, the exact chosen ratio will depend on the nature of the cell sample.

In a preferred embodiment, said vial comprises two compartments. In a preferred embodiment, said compartments of the vial form respectively a hollow platform as the base of said vial, and a column, preferably vertically placed on said platform. Said base of vial may comprise any chosen outline, preferably a round, ellipse, rectangular or square outline. Said platform may be cylindrical, cuboid, conical, parallelepiped, or frustroconical. Said column of the vial may be cylindrical, conical, frustro-conical, parallelepiped, or a cuboid.

In one embodiment, said vial comprises at the base of said first compartment, preferably at the centre of said base, a raised area. Said raised area enhances the flow of the cells from the first to the second compartment, hence ensuring an optimal, high cell density in the latter. Especially for cell sample whereby the analysis with said DHM requires a high cell density or a high number of cells, the latter has been proven to be beneficial. Said raised area may be conical, frustro-conical or hemispherical. Cells may migrate from the first to the second compartment under the influence of gravity alone or a vial comprising a cell sample may be rotated in order to help the cells migrating from the first to the second compartment. Therefore, in a preferred embodiment, the vial is easily rotatable around at least one axis. In a more preferred embodiment, the vial comprises at least one axis of rotational symmetry around which the vial can be easily rotated. In a preferred embodiment, said raised area has a shape which is capable of magnifying the image of objects located in said first compartment. In a more preferred embodiment, said raised area comprises a lens-shaped form. Said raised area has an inner surface which preferably bulges inward in the first compartment, and preferably comprises a form whose width near the base of said first compartment is wider than its width further away from said base. More preferably, said raised area comprises an outer surface which is flat, which bulges inward into said first compartment, and/or bulges outward from said compartment, said outer surface preferably comprising a shape suitable for magnifying the image of objects located in said first compartment. In an even more preferred embodiment, said first compartment comprises a liquid medium with a pre-determined medium refraction index and said lens-shaped form comprises at least one curved surface capable of magnifying the image of objects located in said first compartment with a magnification factor depending on said medium refraction index and said curved surface, whereby preferably said magnification factor is pre-fixed and said medium refraction index and/or said cured surface are adapted to result in said pre-fixed magnification factor.

Preferably, said screening surfaces comprise an optically transparent material, whereby said optically transparent material is to be understood as being transparent to light with wavelengths equal to or in the range of the wavelengths of the illumination means of said DHM. Such material can be, but is not limited to glass, plastic, polycarbonate, certain polymers such as polymethylmethacrylaat (PMMA), polystyrene crystals, polycrystalline materials. It should be clear to an artisan skilled in the art that the latter are mere examples, and that other possibilities are readily known. Optionally said material is further treated by for instance a positively charged surface coating such as poly-L-lysine, or by exposing the surface to a plasma treatment, or treated with anti-reflective substances. Preferably, said vial is obtained by extrusion or co-moulding.

In another, preferred embodiment, said sample comprises supporting means at said base of vial. Said supporting means support vial when placed on a surface and prevent said screening surfaces of vial from coming into contact with said surface. The latter prevents said screening surfaces from being scratched or stained by the surface which can cause aberrant or divergent scanning from deviation of the beams of the DHM. Said supporting means may comprise, but are not limited to an upstanding rim at the circumference of the base of said vial or supporting feet at distinct positions of said circumference. Said supporting means may be produced of any material known to artisan skilled in the art, such as plastic, glass or rubber.

In another embodiment, said second compartment can comprise means for evacuating air bubbles. Air bubbles are to be avoided during screening, as the later can cause aberrant analysis. For an adequate and reliable analysis, said second vial should be filled entirely with fluid sample. In one embodiment, said means for discharging air bubbles can comprise grooves, provided at said bottom of said second compartment. Said grooves aid to evacuate any air bubbles present in said second compartment, preferably in the direction of the first compartment and/or the outer environment.

In a preferred embodiment, said vial comprises an opening, preferably said opening is located at the first compartment, in a most preferred embodiment said first compartment being the column. In a preferred embodiment, said opening is capable of engaging with a lid in order to make said vial liquid-tight. In the current invention, the term 'liquid-tight' is to be understood as not allowing any passage or spillage of sample fluid from the inner side of the sample to the outer environment. Said lid preferably comprises a snap-on cap, a friction-fit or a threaded screw-cap. In a more preferred embodiment, said lid comprises an optically transparent material, whereby said material is only optically transparent for light with wave lengths equal to these from the illumination means of DHM and partially or not optically transparent for light with other wavelengths. The latter allows transmission of said illumination beam of DHM and illumination of said sample inside liquid-tight vial. In one embodiment, said lid is entirely produced of an optically transparent material. In another embodiment, said lid is only partially produced from an optically transparent material. In yet another embodiment, said only one specific side or section, such as for instance a window, of said lid is produced from an optically transparent material.

In a preferred embodiment, said opening of first compartment provides for an entrance for receiving a cell collecting device. Said cell collecting device is used for collecting a cell sample from an organism, preferably a human, or for transferring a part of a cell sample stored in a first vial, to a sample vial of the current invention. The cell collecting device may comprise a brush, a spatula, a cotton swab, a needle, a scraper, a pipette or a Pasteur pipette. Preferably, said cell collection device comprises means for collecting a sample, such as a brush, a spatula or a cotton ball, engaged to a longitudinal handle. More preferably, said means for collecting cells is attachable to said longitudinal handle by a snap-release joint as described in EP 2 263 552. The latter allows said means for collecting cells to disengage after collecting the cells from the handle with a simple exertion of pressure. In an embodiment of the invention the means for collecting cells are positioned against a surface inside a sample vial, preferably one of the walls of the first compartment of said vial. This has for effect that the cell collection device can be transferred to a fixation fluid, prior to the disconnection of the sampling head from the longitudinal handle.

By allowing the collected cells ample to be transferred directly from the origin or site of sampling to the sample vial, the transfer of sampled cells is maximized; ease of handling enlarged and the risk of losing cells is reduced.

In a preferred embodiment, said vial comprises means for aiding the disengagement of means for collecting cells from said cell collection device. Preferably, said means for aiding the disengagement are provided to the wall of a compartment, preferably said compartment is the first compartment. Said means for aiding the disengagement may comprise one or more wall protrusions such as for instance pins, and/or one or more wall indentations.

In a preferred embodiment, said fluid connection between said compartments prevents said cell collecting device, more specifically said means for collecting cells, from entering the second compartment of said vial.

In a more preferred embodiment, said vial comprises a sub-compartment for receiving means for collecting cells. Said sub-compartment, is preferably present in the first compartment of said sample vial. The sub-compartment is specifically designed to receive means for collecting cells and retaining said means therein. This prevents said means from freely floating in the vial, thereby possibly obstructing the illumination beams of the DHM when screening through the pair of screening surfaces, hence causing distortion in the analysis. Preferably, said sub-compartment encompasses said means for aiding the disengagement of means for collecting cells.

Said sub-compartment is in liquid connection with the other compartments of said vial. Preferably, said liquid connection is provided by an opening, connecting said sub-compartment with other compartments, or more preferably by a filter membrane, delineating one or more sides of said sub-compartments. Preferably, said filter membrane is designed to ensure passage of both liquid and cells, simultaneously preventing passage of cell debris, tissue clumps and/or mucus. Preferably, said filter membrane comprises a mesh which pore size is optimized for the latter.

Preferably, when said sample vial is provided with a sub-compartment for receiving means for collecting cells and with a lid for making vial liquid-tight, said lid is only partially produced of an optically transparent material, preferably at one side or one section of said lid, such as a window. Preferably, said side or section produced of an optically transparent material is located opposite from said sub-sub-compartment for receiving means for collecting cells, when said lid is engaged in a liquid-tight manner to said vial.

Alternatively, in another preferred embodiment, said vial is internally provided with a filter membrane, whereby said filter membrane is located at either the first compartment or at the fluid connection of said first and second compartment. Preferably, said filter membrane will span an entire section of said first compartment or section determining fluid connection between said first and second compartment. Said filter membrane ensure passage of cells and liquid, but prevent passage of mucus, cell debris and tissue particles, which are undesirable during screening by DHM.

In another preferred embodiment, said sample vial comprises identifying indicia, said indicia may be fixed indicia and/or programmable indicia. Said indicia can correlate to type of sample, information on the origin of sample such as patient identity, general patient ID info (e.g. age, gender, residential area, . . . ), sample information (e.g. place and time when the sample was taken), owner ID info (e.g. the name of the user/institution from which the info comes from), DHM-ID info (e.g. a serial number of the DHM with which the DHM-obtained object properties are measured or observed), etc. or any combination thereof. Said identifying indicia are preferably machine-readable. In one embodiment, said indicia comprise a bar code label, which corresponds to and uniquely identifies the vial and the sample contained therein. In a most preferred embodiment, said indicia comprise an RFID tag. The indicia are read by identifying means, such as a laser scanner bar code reader in the case of the indicia being a bar code, or an RFID reader when indicia being an RFID tag. Additionally, information related to the date and time of the obtained holographic information can be added, in addition to the initial sample indicia. Optionally, the name or other identifier of the cytological laboratory analyzing the sample with the system may be linked to the identification information as well.

In another embodiment, said vial comprises a solution, preferably a preservative. Said preservative is a preserving solution and/or fixative for the collected cells. Said preservative preferably comprises a buffering component, an alcohol and/or an anti-clumping agent. Such preservatives are known in prior art and hence, their exact composition should be clear to any person skilled in the art. Furthermore, supplementation of other additives, such as coloring agents, cell markers etc. to the preservative is equally possible and will rely on the nature of the cell sample and/or the purpose of the analysis. Preferably, said sample vial are prefilled with preservative solution prior to vending.

In a second aspect of the current invention, the invention comprises a method for analyzing a liquid cell sample by digital holographic microscopy (DHM). Said method comprises the following steps:
  obtaining a cell sample;
  preserving said cell sample in a sample vial according to the current invention;
  providing a digital holographic microscope;
  obtaining parameters and images of cell sample by means of DHM,
characterized in that said DHM obtains parameters and images by screening said sample in the first and/or second compartment of said vial via a scanning-pattern.

Said scanning pattern may comprise a random line-pattern, a non-periodically line-pattern, a periodically line-pattern, a continue or discontinue pattern, a zigzag pattern, a line-pattern with phase and amplitude etc. Said screening the sample via a line-pattern ensures that the DHM will scan only unique sections of said sample, hence preventing that one section is screened multiple times. The latter ensures that significantly reliable and adequate information is obtained from said cell sample. Preferably, when a sufficient amount of cells is screened by said DHM, hence gathering enough information for a reliable analysis, said screening will be automatically stopped.

In a preferred embodiment, obtaining said cell sample occurs by cell collecting device.

In another aspect, the current invention reveals a system for analyzing a liquid cell sample. Said system comprises a digital holographic microscope and at least one sample vial according to the current invention, characterized in that system comprises means for screening said sample via a scanning pattern. Preferably, said means may comprise a movable platform or sample vial holder, whereby said platform or holder will move said sample vial during analysis of said sample. Preferably, said movement involves a rotational movement. In another embodiment, said means may comprise a movable lens, movable illumination means of said DHM or means that can alter the pathway of said illumination means such as for instance a mirror.

The invention is further described by the following non-limiting examples which further illustrate the invention, and are not intended to, nor should they be interpreted to, limit the scope of the invention.

EXAMPLES

Figure 1B:
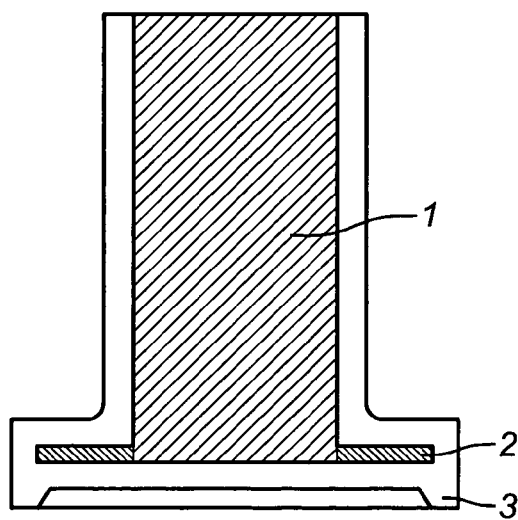
Figure 6A:
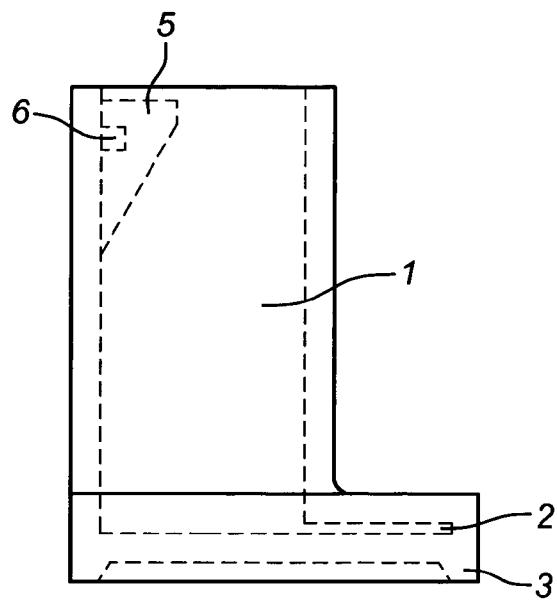
Figure 6B:
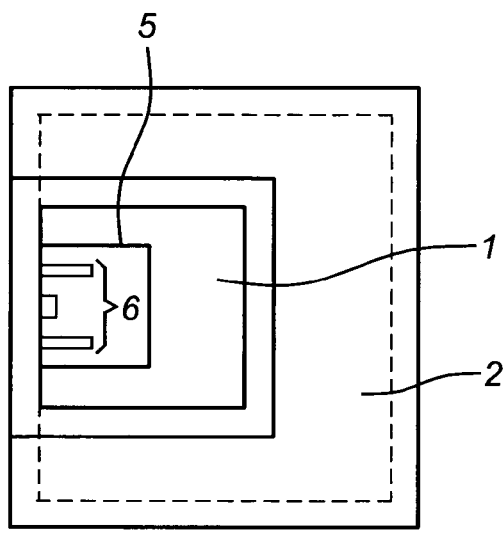
Figure 7A:
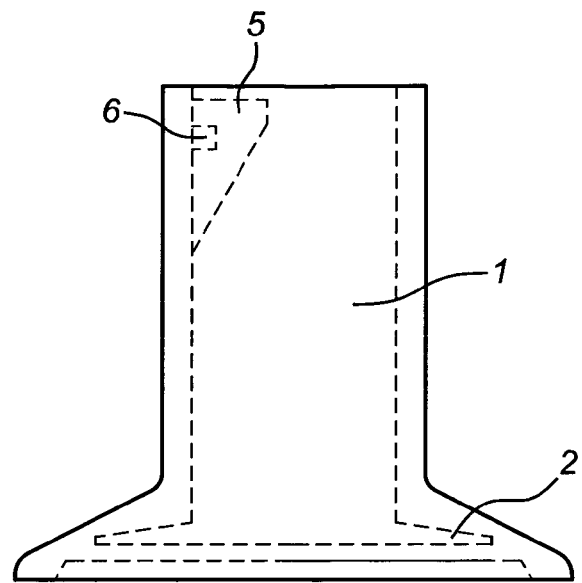
Figure 7B:
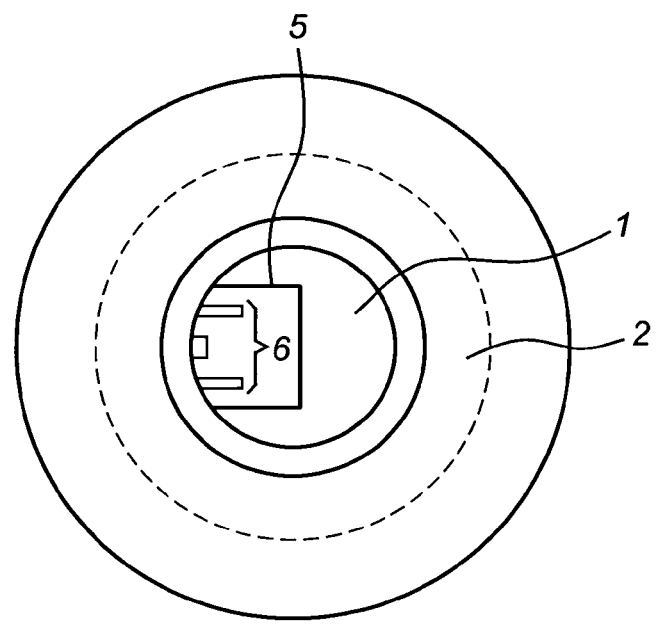
Figure 9A:
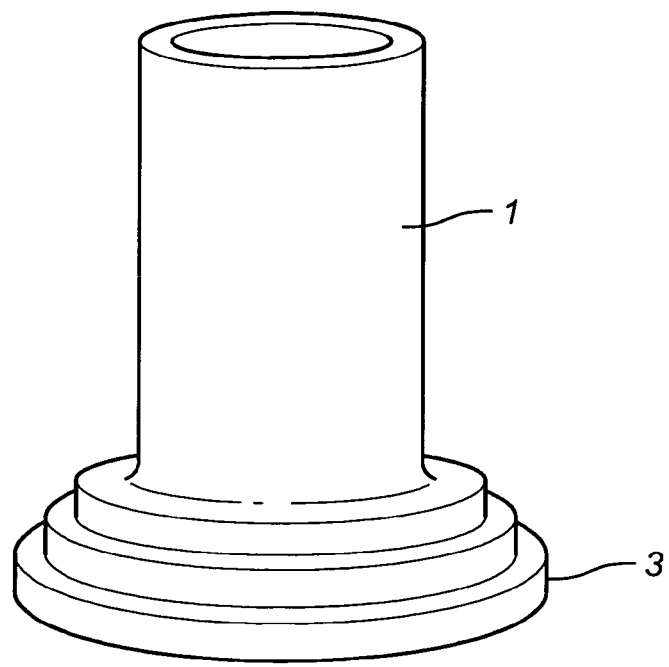
Figure 9B:
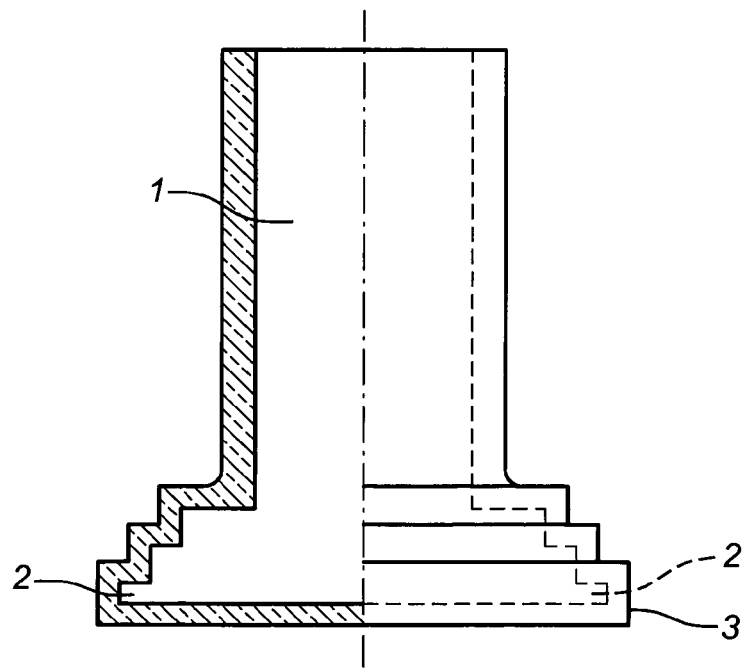

FIGS. 1 to 7 depict preferred embodiments of the sample vial according to the current invention. Said sample vial comprises a first (1) and second (2) compartment, whereby said first (1) and second (2) compartment are in liquid connection with one other and whereby each said compartment comprises a pair of screening surfaces. The shading pattern in FIG. 1b defines further the meaning of said first (1) and second compartment (2). For instance, said sample vial may be T-shaped, comprised of cylindrical compartments as shown in FIG. 1, or comprised of cuboids (FIG. 5) or comprised of a combination of cylindrical and frustro-conical compartments (as shown in FIG. 7). Alternatively, said vial may be L-shaped, as shown in FIG. 6. FIG. 9 shows another possible embodiment of the invention, whereby said sample vial comprises a first compartment at the base, which has a step-wise appearance.

Figure 2A:
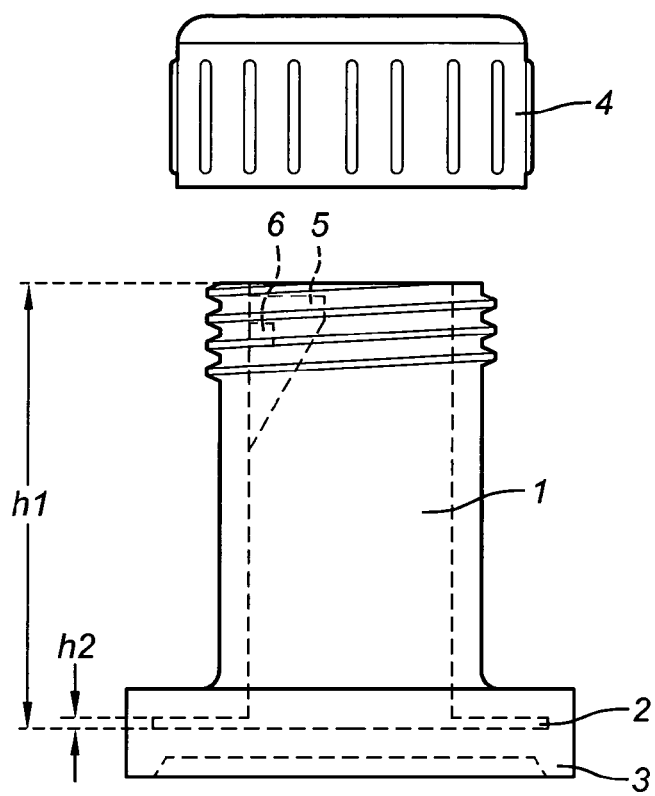
Figure 3:
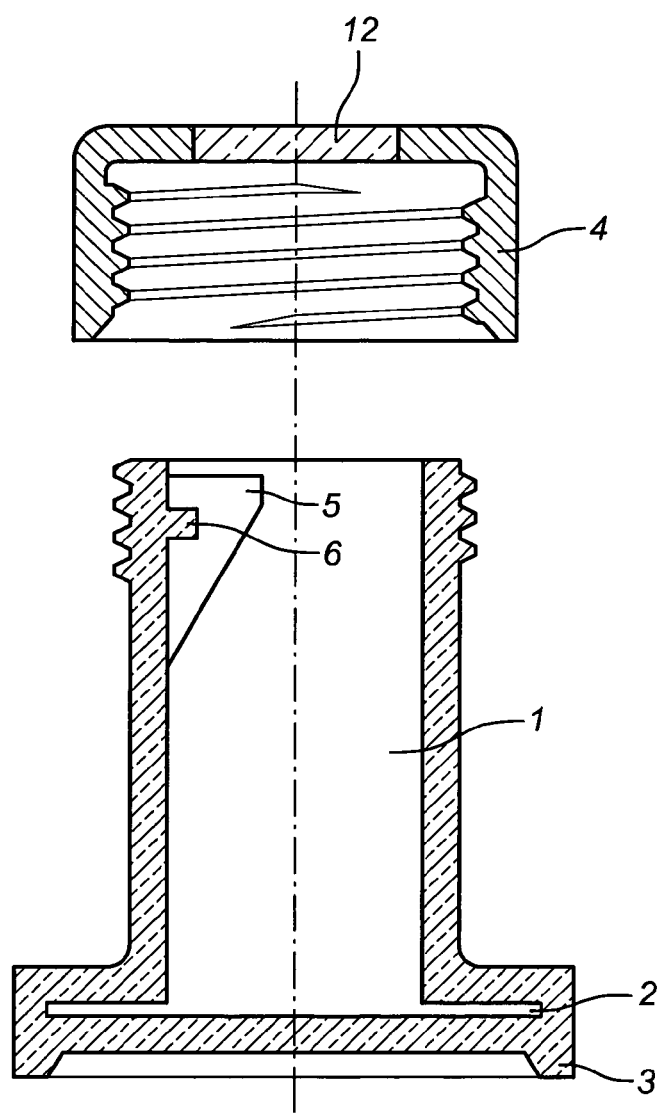

As shown in FIGS. 2a and 3, the vial may be provided with a lid (4), making said vial liquid-tight when said lid is engaged to said vial. Preferably said lid (4) is a screw cap. Said vial may comprise an optically transparent material, whereby said optically transparent material may be restricted to for instance only a section of said lid. The lid (4) of the sample vial as depicted in FIG. 3 comprises a window (12), comprised of optically transparent material. Said window allows screening of the sample by DHM through the lid (4).

The sample vial is preferably foreseen of supporting means (3) at the base of the vial, for providing support when placed on a surface. Said supporting means (3) prevent the screening surfaces at the base of the vial from being scratched and/or stained.

Figure 8A:
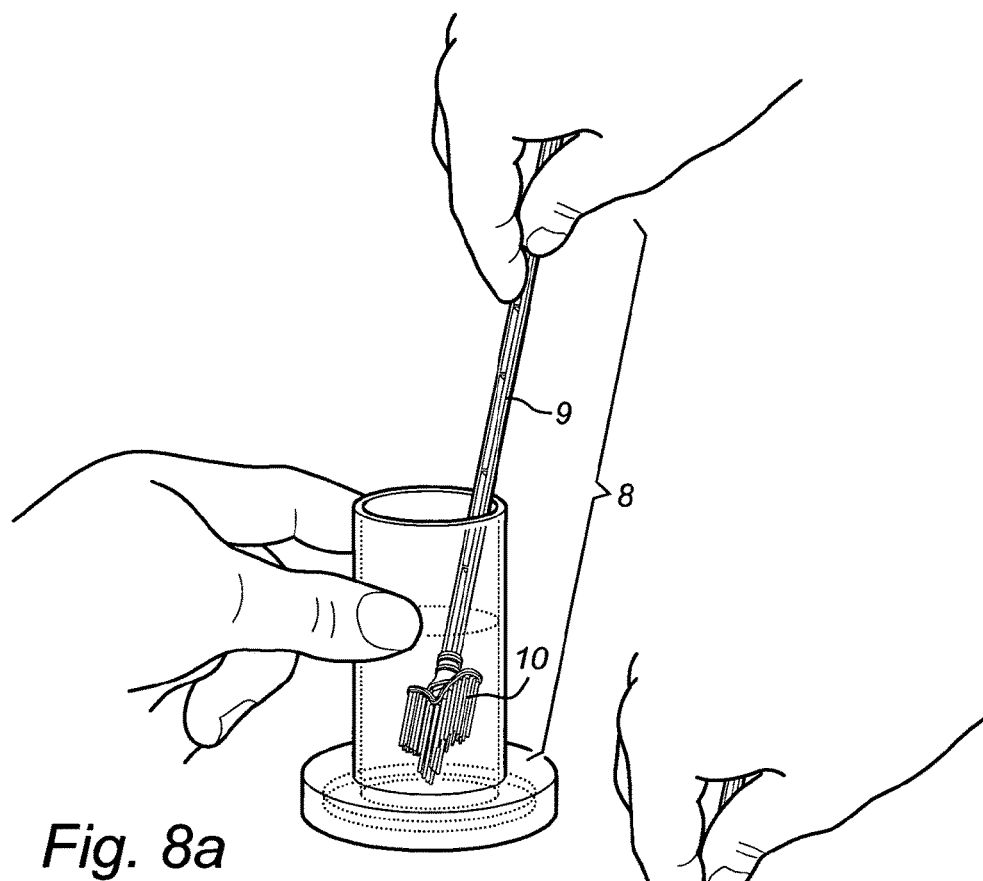
FIG. 8 shows exemplary ways of providing a cell sample collected by a cell collecting device to a sample vial according to an embodiment of the current invention.
Figure 8B:
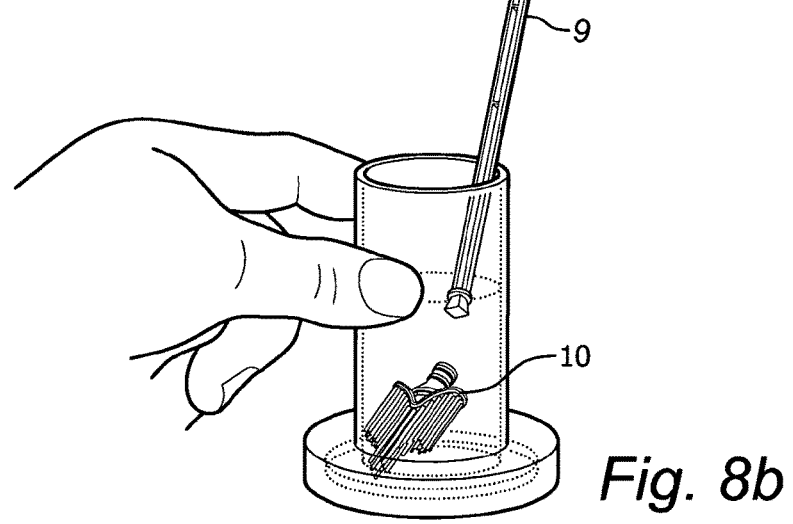
Figure 8C:
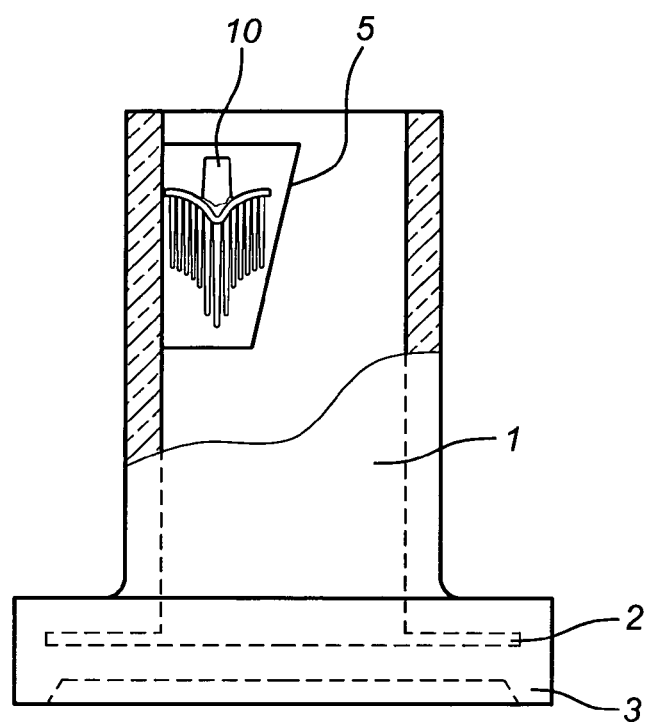

For specific purposes, the vial may be equipped with a sub-compartment (5) and/or means for aiding the disengagement (6) of means for collecting cells (10) from a cell collection device (8) and the handle (9) of the cell collection device (8). The means for aiding the disengagement may be, as shown in FIGS. 2 to 7, protrusions (6) extending from the wall of the first compartment (1). In the current example, these protrusions will help a practitioner with the disengagement of a sample brush (10) from a longitudinal handle and is preferably encompassed by a sub-compartment (5). This sub-compartment is designed to receive the sample brush (10) or any other means for collecting cells. As shown in FIG. 8, there exist multiple ways of providing the collected cells from a cell collecting device (8) to the sample vial. The cells may be provided by a stirring movement of the device (8) as shown in FIG. 8a. Through the stirring, the collected cells will 'fall' from the brush (10) and disperse in the preservative solution provided in the sample vial. Alternatively, the means for collecting cells (10), in the current example a brush, will be disconnected from the handle (9), leaving the brush at the bottom of the first compartment of the vial (see FIG. 8b). The fluid connection between the first and second compartment will prevent the brush from entering the second compartment. Another option is shown in FIG. 8c, whereby the sample vial is provided in the first compartment with a sub-compartment (5), for receiving and retaining the brush (10), after the latter is released from the handle (9). The sub-compartment (5) and brush (10) remains in fluid connection with the first compartment, allowing the collected cells to migrate from the sub-compartment to the first and second compartment. Preferably, this connection is ensured by a filter membrane delineating the sub-compartment (5) or an opening in said sub-compartment (5).

Figure 4:
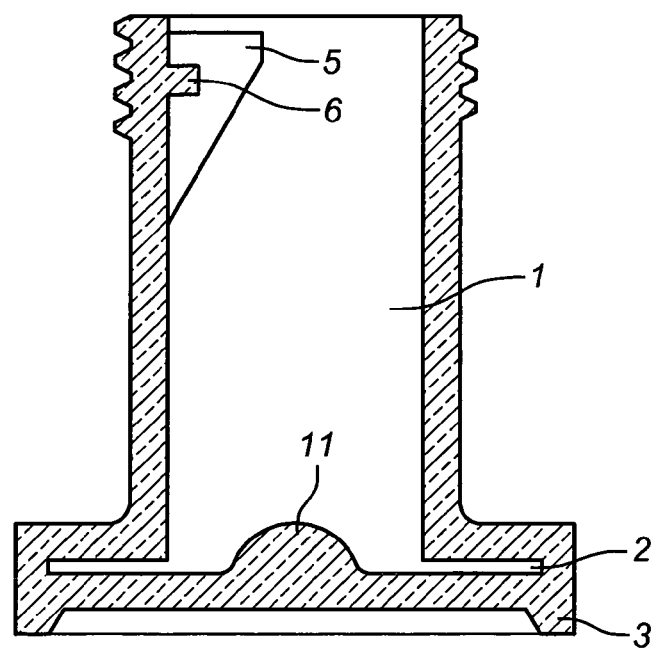
Figure 5A:
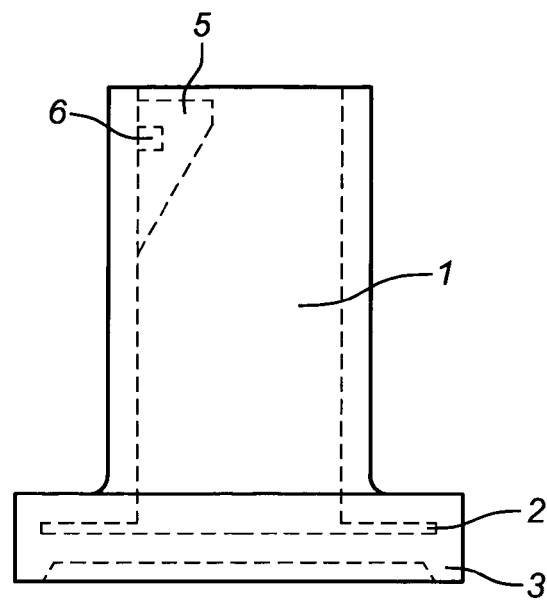
Figure 5B:
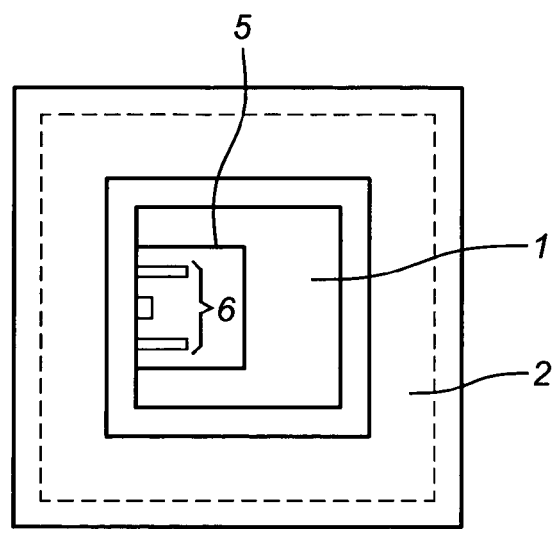

As shown in FIG. 4, the base of the first compartment (1) of the vial may at the inner side be accommodated with a raised area (11). The raised area (11) enhances the flow of the cells from the first to the second compartment, hence ensuring an optimal, high cell density in the latter.

As shown in FIG. 2a, the distance (h2) between the pair of screening surfaces of the second compartment (2) is smaller than the distance (h1) between the pair of screening surfaces of the first compartment (1). This is important as the latter will provide different cell densities in both compartments. Dense cell layers, comprising a few layers or even only one layer of cells will be achieved in the second compartment, whereas lesser dense layers will be achieved in the first compartment (1).

Figure 2B:
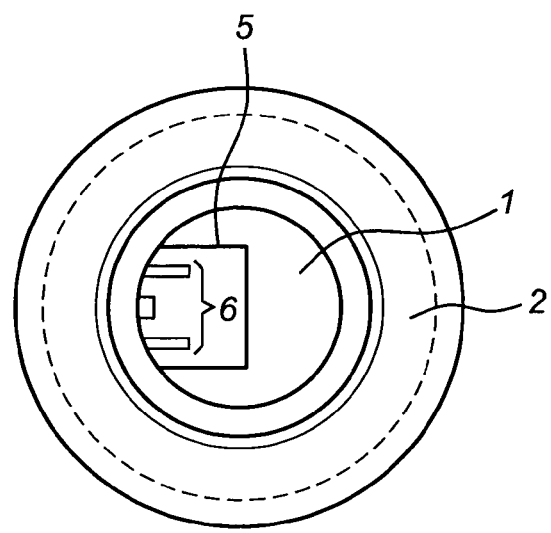

For instance, a sample vial as shown in FIG. 1 or FIG. 2, suitable for the screening of a cervical cell sample by DHM, may comprise the following dimensions:
h1: 42 mm
h2: 1 mm
surface area A1: ±452 mm$^2$
surface area A2: ±1537.34 mm$^2$

What is claimed is:

1. A sample vial for receiving a liquid cell sample, to be used in conjunction with a digital holographic microscope (DHM), said sample vial having an upper and lower end and comprising at least two compartments in fluid connection with one another, of which a first compartment comprises a column and a second compartment forms a base at the lower end of said vial, wherein the first compartment comprises a first upper screening surface and a first lower screening surface, and the second compartment comprises a second upper screening surface and a second lower screening surface, wherein said screening surfaces are flat,
    wherein the first upper and first lower pair of screening surfaces define a field of view different from the second upper and second lower screening surfaces, and
    wherein the distance between the second upper and second lower screening surfaces is smaller than the distance between the first upper and first lower screening surfaces, wherein a ratio of the distance between said first upper and lower screening surfaces to said second upper and lower screening surfaces is between 200:1 and 20:1 and/or the ratio of the surface area of the first upper or lower screening surface to the second upper or lower screening surface is between 1:1000 and 50:1.

2. The sample vial according to claim 1, wherein said screening surfaces comprise an optically transparent material.

3. The sample vial according to claim 1, wherein said vial comprises a lid, making vial liquid-tight when engaged to said vial.

4. The sample vial according to claim 3, wherein said lid comprises an optically transparent material.

5. The sample vial according to claim 1, wherein said first compartment comprises an entrance for receiving a cell collecting device.

6. The sample vial according to claim 5 whereby said fluid connection between said compartments prevents said cell collecting device from entering said second compartment.

7. The sample vial according to claim 5, wherein said vial comprises one or more protrusions on and/or one or more indentations in a wall of a compartment of the vial.

8. The sample vial according to claim 5, wherein said first compartment comprises a sub-compartment for receiving and retaining a cell collecting system.

9. The sample vial according to claim 1, further comprising an upstanding rim at the circumference of the base of said vial or supporting feet at distinct positions of said circumference of the base of said vial.

10. The sample vial according to claim 1, further comprising an identification tag.

11. The sample vial according to claim 1, further comprising a preservative.

12. The sample vial according to claim 1, wherein said vial is internally provided with a filter membrane.

13. The sample vial according to claim 12, wherein the filter membrane ensures passage of both liquid and cells, simultaneously preventing passage of cell debris, tissue clumps and/or mucus.

14. A method for analyzing a liquid cell sample by digital holographic microscopy (DHM), comprising the steps of:
    obtaining a cell sample;
    preserving said cell sample in a sample vial according to claim 1;
    providing a digital holographic microscope;
    obtaining parameters and images of the liquid cell sample by DHM,
wherein said DHM obtains parameters and images by screening said sample in the first and/or second compartment of said vial via a scanning pattern.

15. A system for analyzing a liquid cell sample comprising a digital holographic microscope and at least one sample vial according to claim 1, wherein the system comprises a movable platform or sample vial holder, a movable lens, and a movable light source of said DHM or illumination-pathway altering system for screening said sample via a scanning pattern.

* * * * *

UNITED STATES PATENT AND TRADEMARK OFFICE
CERTIFICATE OF CORRECTION

PATENT NO. : 9,846,151 B2  
APPLICATION NO. : 14/359556  
DATED : December 19, 2017  
INVENTOR(S) : Olivier Magniette It is certified that error appears in the above-identified patent and that said Letters Patent is hereby corrected as shown below:

In the Specification

In Column 8 at Line 29, Change "frustroconical." to --frustoconical.--.

In Column 8 at Line 30, Change "frustro-conical," to --frusto-conical,--.

In Column 8 at Line 40, Change "frustro-conical" to --frusto-conical--.

In Column 9 at Line 10, Change "polymethylmethacrylaat" to --polymethylmethacrylate--.

In Column 12 at Lines 37-38, Change "frustro-conical" to --frusto-conical--.

In the Claims

In Column 13 at Line 57, In Claim 1, after "lower" delete "pair of".

Signed and Sealed this  
First Day of May, 2018

Andrei Iancu  
*Director of the United States Patent and Trademark Office*